United States Patent
Sato

(10) Patent No.: US 11,083,483 B2
(45) Date of Patent: Aug. 10, 2021

(54) TISSUE EXCISION INSTRUMENT

(71) Applicant: OLYMPUS CORPORATION, Hachioji (JP)

(72) Inventor: Keiichi Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 34 days.

(21) Appl. No.: 16/658,574

(22) Filed: Oct. 21, 2019

(65) Prior Publication Data

US 2020/0046400 A1 Feb. 13, 2020

Related U.S. Application Data

(63) Continuation of application No. PCT/JP2017/018861, filed on May 19, 2017.

(51) Int. Cl.
*A61B 17/3205* (2006.01)
*A61B 17/32* (2006.01)

(52) U.S. Cl.
CPC .......... *A61B 17/32056* (2013.01); *A61B 17/320016* (2013.01)

(58) Field of Classification Search
CPC ...... A61B 17/32056; A61B 2017/2212; A61B 10/02; A61B 10/0266; A61B 17/26
See application file for complete search history.

(56) References Cited

U.S. PATENT DOCUMENTS

2005/0096650 A1   5/2005   Ouchi

FOREIGN PATENT DOCUMENTS

| JP | H04-241853 A | 8/1992 |
|---|---|---|
| JP | 2002-253559 A | 9/2002 |
| JP | 2005-130957 A | 5/2005 |
| JP | 4051292 B2 | 2/2008 |
| JP | 4761597 B2 | 8/2011 |
| KR | 2017-0088006 A | 8/2017 |
| WO | 2016/080093 A1 | 5/2016 |

OTHER PUBLICATIONS

Merriam-Webster definition for "intersect" accessed Jan. 30, 2021; https://www.merriam-webster.com/dictionary/intersect.*
Jun. 20, 2017 International Search Report issued in International Patent Application No. PCT/JP2017/018861.
Apr. 27, 2021 Notice of Allowance issued in Japanese Patent Application No. 2019-518716.

* cited by examiner

*Primary Examiner* — Wade Miles
(74) *Attorney, Agent, or Firm* — Oliff PLC

(57) ABSTRACT

A tissue excision instrument that includes a sheath having a lumen, a manipulation member movably disposed inside the lumen, a snare wire coupled to a distal end of the manipulation member, and a holder provided at a distal portion of the sheath and configured to have a through-hole. The snare wire includes a first wire portion that has a first proximal portion including one end and a first distal portion, a second wire portion that has a second proximal portion including the other end and a second distal portion, extends through a through-hole between the second proximal portion and the second distal portion, and extends across the first wire portion, and a curved portion that extends to be curved between the first distal portion and the second distal portion and has at least a part disposed on a distal side relative to the through-hole.

5 Claims, 14 Drawing Sheets

TISSUE EXCISION INSTRUMENT

The present disclosure relates to a tissue excision instrument. This application is a continuation application based on a PCT International Application No. PCT/JP2017/018861. The content of the PCT International Application is incorporated herein by reference.

BACKGROUND

In the past, snares have been used to excise tissue in the digestive tract such as polyps. For example, as shown in Japanese Patent No. 4051292 and Japanese Patent No. 4761597, a snare has a sheath, a manipulation wire that is inserted into the sheath to move in an axial direction, and a snare loop that is formed of an elastic wire coupled to the manipulation wire. The snare loop is formed by bending back a single elastic wire at a distal end thereof. The snare loop can protrude or retreat at a distal end of the sheath when the manipulation wire is advanced or retracted in the axial direction. In a state where the snare loop protrudes from the distal end of the sheath, the snare loop swells due to its own elasticity. The snare loop is pulled into the sheath in this state, and the snare loop shrinks.

When the snare is in use, the snare loop is hooked on target tissue that is a target to be excised such as a polyp, and then the manipulation wire is pulled. Thus, the target tissue is constricted by the snare loop and is excised from the digestive tract.

SUMMARY

A tissue excision instrument can include a sheath configured with a lumen extending along a longitudinal axis and a manipulation member that also extends along the longitudinal axis. The manipulation member is provided in the lumen to be movable along the longitudinal axis. The tissue excision instrument can also include a snare wire coupled to a distal end of the manipulation member. The snare wire can protrude from the sheath such that an amount of protrusion from the sheath is adjusted depending on movement of the manipulation member. The tissue excision instrument can also include a holder provided at a distal portion of the sheath and it can be configured to include a through-hole that opens in a direction intersecting the longitudinal axis. The snare wire can include a first wire portion that has a first proximal portion including one end of the snare wire and a first distal portion linked to the first proximal portion, a second wire portion that has a second proximal portion including the other end of the snare wire and a second distal portion linked to the second proximal portion, extends through the through-hole between the second proximal portion and the second distal portion, and extends across the first wire portion, and a curved portion that extends to be curved between the first distal portion and the second distal portion, is linked to the first distal portion and the second distal portion, and has at least a part disposed on a distal side relative to the through-hole.

DETAILED DESCRIPTION

Figure 1:
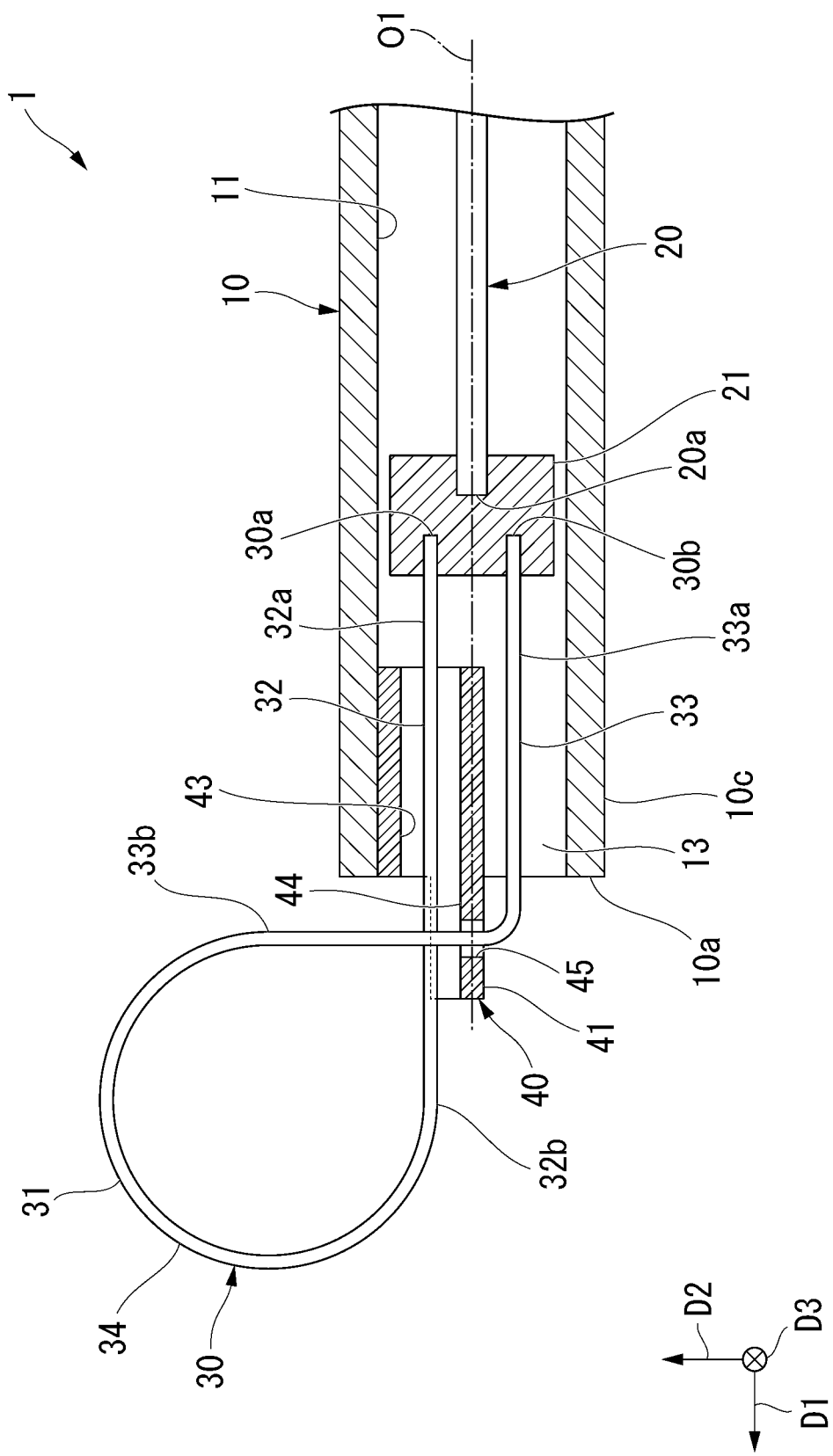
FIG. 1 is a side sectional view showing a distal end side of a snare according to an exemplary embodiment.
Figure 2:
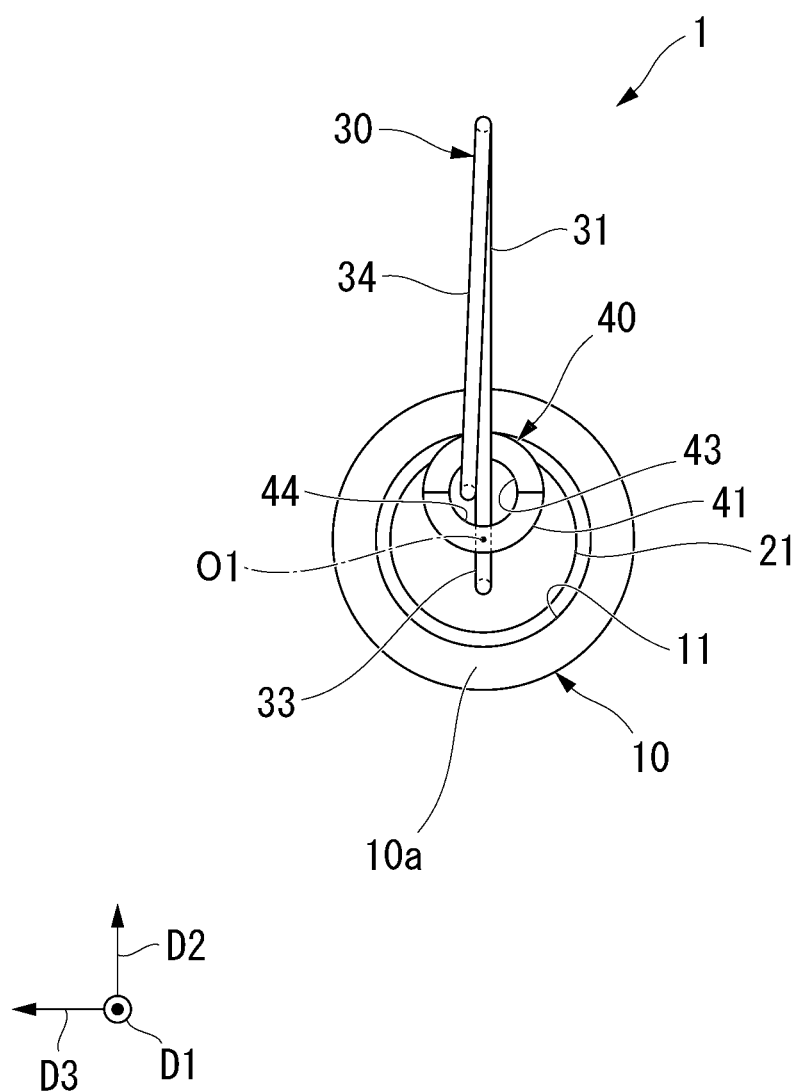
FIG. 2 is a front view showing the distal end side of the snare.
Figure 3:
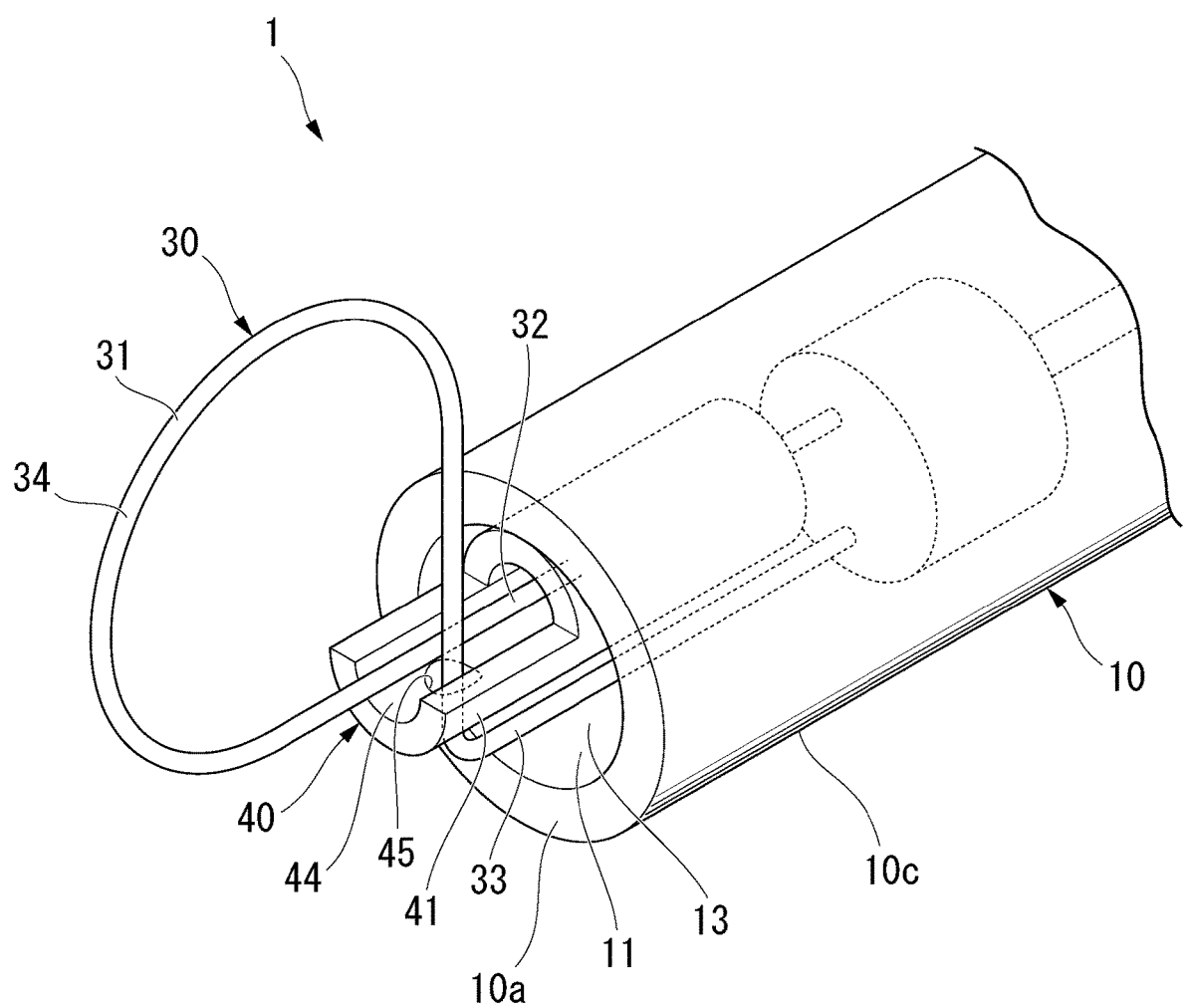
FIG. 3 is a perspective view showing the distal end side of the snare.
Figure 3:
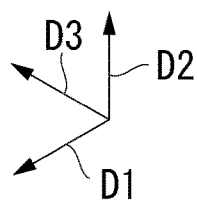
Figure 4:
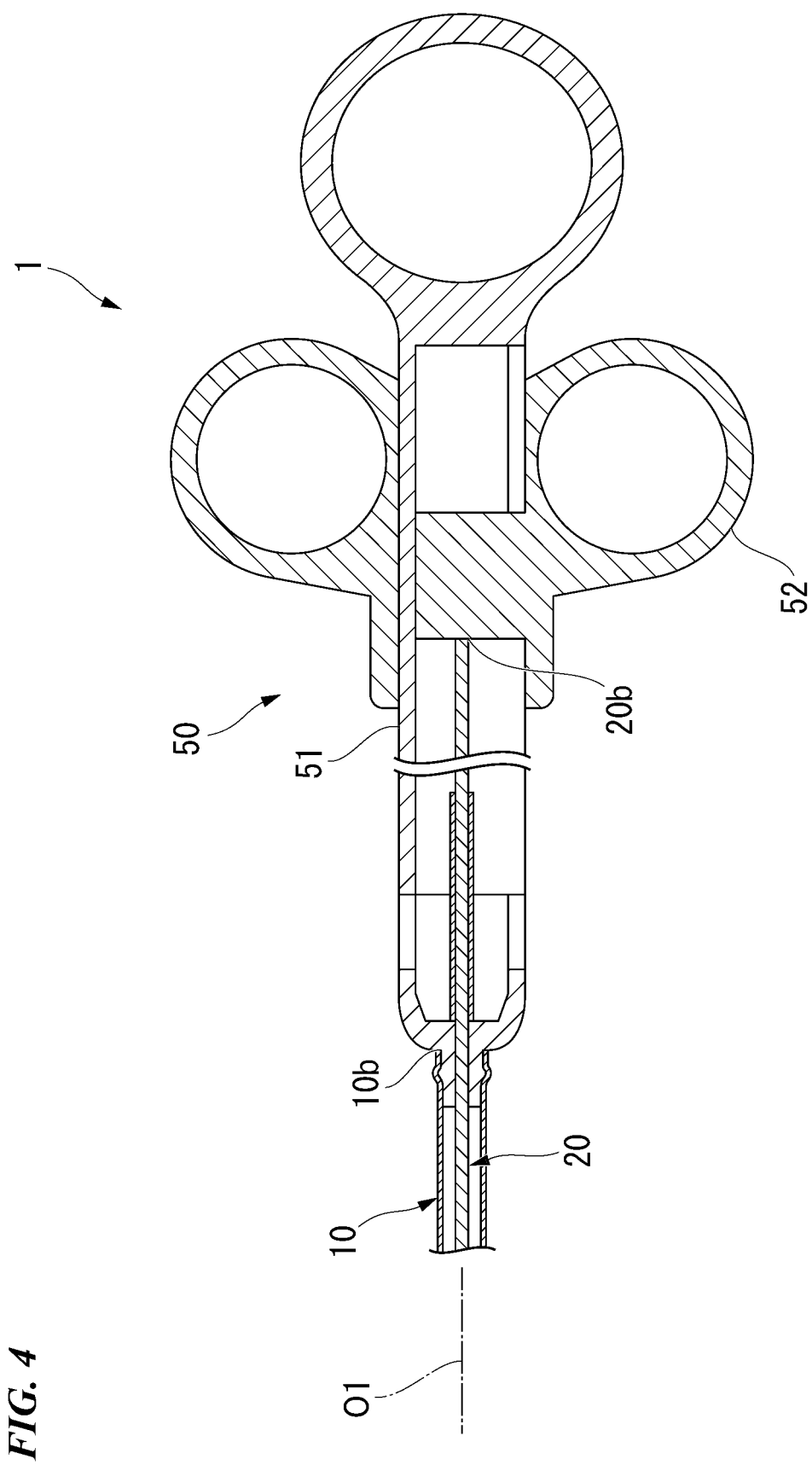
FIG. 4 is a side sectional view showing a proximal end side of the snare.

FIG. 1 is a side sectional view showing a distal end side of a snare 1 that is a tissue excision instrument according to the present embodiment. FIG. 2 is a front view showing the distal end side of the snare 1. FIG. 3 is a perspective view showing the distal end side of the snare 1. FIG. 4 is a side sectional view showing a proximal end side of the snare 1. As showned in FIGS. 1 to 4, the snare 1 includes a sheath 10, a manipulation wire (a manipulation member) 20, a snare wire 30, and a holder 40. The snare 1 is used along with a well-known endoscope (not shown).

The sheath 10 extends along a longitudinal axis O1 and is formed to be long. In the present embodiment, the sheath 10 is formed in a columnar shape, a central axis of which is a longitudinal axis O1. The sheath 10 has flexibility and is configured to be insertable/extractable into/from a treatment tool channel (not shown) of an endoscope. An outer diameter of the sheath 10 is set to be smaller than an inner diameter of the treatment tool channel, and a length of the sheath 10 in an axial direction is set to be longer than that of the treatment tool channel in an axial direction. The sheath 10 has a lumen 11 thereinside. The lumen 11 extends from a distal end 10a to a proximal end 10b of the sheath 10 along the longitudinal axis O1, and opens at the distal end 10a of the sheath 10. In the present embodiment, the lumen 11 is formed in a columnar shape, a central axis of which is the longitudinal axis O1, and is disposed coaxially with the sheath 10. Further, a manipulator 50 is coupled to the proximal end 10b of the sheath 10. The sheath 10 is formed of, for example, a fluororesin such as polytetrafluoroethylene (PTFE).

In the following description, a direction that is oriented from a proximal end side to a distal end side of the sheath 10 along the longitudinal axis O1 is appropriately referred to as a first direction D1. A direction that is parallel to an axis perpendicular to the longitudinal axis O1 is appropriately referred to as a second direction D2. A direction that is parallel to an axis perpendicular to both the first direction D1 and the second direction D2 is appropriately referred to as a third direction D3. Further, a distal end side along the longitudinal axis O1 is also appropriately referred to as a distal side, and a proximal end side along the longitudinal axis O1 is also appropriately referred to as a proximal side.

The manipulation wire 20 extends along the longitudinal axis O1, and is disposed inside the sheath 10 to be movable along the longitudinal axis O1. In the present embodiment, the manipulation wire 20 is movably inserted into the lumen 11 of the sheath 10. Further, the manipulation wire 20 extends from the vicinity of the distal end 10*a* of the sheath 10 past the proximal end 10*b* of the sheath 10 to the manipulator 50. An outer diameter of the manipulation wire 20 is set to be smaller than a diameter (an inner diameter) of the lumen 11 of the sheath 10. The manipulation wire 20 is formed of, for example, a metal wire made of stainless steel or the like.

The snare wire 30 is coupled to a distal end 20*a* of the manipulation wire 20. The snare wire 30 protrudes from the sheath 10, and is configured such that an amount of protrusion from the sheath 10 is adjusted depending on the movement of the manipulation wire 20. Further, the snare wire 30 includes a first wire portion 32, a second wire portion 33, and a curved portion 34. The first wire portion 32 has a first proximal portion 32*a* that includes a first end (one end) 30*a* of the snare wire 30, and a first distal portion 32*b* that is linked to the first proximal portion 32*a*. The second wire portion 33 has a second proximal portion 33*a* that includes a second end (the other end) 30*b* of the snare wire 30, and a second distal portion 33*b* that is linked to the second proximal portion 33*a*. The curved portion 34 extends to be curved between the first distal portion 32*b* and the second distal portion 33*b*, and is linked to the first distal portion 32*b* and the second distal portion 33*b*.

The snare wire 30 can be made of a single elastic wire. The elastic wire is formed of, for example, a stranded wire of a stainless steel wire. The first and second ends 30*a* and 30*b* of the snare wire 30 are coupled to the distal end 20*a* of the manipulation wire 20 via a coupler 21. The coupler 21 is formed in a columnar shape whose central axis is the longitudinal axis O1, and is movably disposed inside the lumen 11 of the sheath 10. An outer diameter of the coupler 21 is set to be slightly smaller than a diameter of the lumen 11. The first and second ends 30*a* and 30*b* of the snare wire 30 are inserted into a distal end of the coupler 21, and are fixed to the coupler 21 by brazing or welding. A position at which the first end 30*a* of the snare wire 30 is inserted and a position at which the second end 30*b* of the snare wire 30 is inserted are spaced from each other at the distal end of the coupler 21. Further, the distal end 20*a* of the manipulation wire 20 is inserted into the proximal end of the coupler 21, and is fixed to the coupler 21 by brazing or welding.

The holder 40 is provided at a distal portion 10*c* of the sheath 10. Further, the holder 40 has a through-hole 45 that opens in a direction in which it intersects the longitudinal axis O1. In the present embodiment, the through-hole 45 opens in the second direction D2 perpendicular to the longitudinal axis O1.

The holder 40 can be formed in a cylindrical shape that extends along the longitudinal axis O1. The holder 40 has a hollow forming surface 43 that forms a hollow space extending along the longitudinal axis O1 inside the holder 40. An outer diameter of the holder 40 is set to be smaller than the diameter of the lumen 11 of the sheath 10. An inner diameter of the holder 40 is set to be larger than the outer diameter of the snare wire 30.

The holder 40 is disposed on a distal end side relative to the coupler 21 such that an axis of the holder 40 is approximately parallel to the longitudinal axis O1. Further, the holder 40 is disposed in the lumen 11 such that a part thereof protrudes from the distal end 10*a* of the sheath 10. A portion of the holder 40 which protrudes from the distal end 10*a* of the sheath 10 toward the distal end side constitutes a semicylindrical distal portion 41 where the upper half in the second direction D2 (in the radial direction of the sheath 10) is opened and a part of the hollow forming surface 43 is exposed as an exposed surface 44. The through-hole 45 passes between the exposed surface 44 and an outer circumferential surface of the holder 40 at the distal portion 41. The through-hole 45 is disposed at a position that is on the distal end side relative to the distal end 10*a* of the sheath 10 and is on the proximal end side relative to the distal end of the holder 40. An inner diameter of the through-hole 45 is set to be slightly larger than the outer diameter of the snare wire 30.

Further, the holder 40 is disposed in contact with an inner surface of the lumen 11 (an inner surface of the sheath 10), and a portion of the holder 40 which is in contact with the lumen 11 has at least a part fixed to the inner surface of the lumen 11 by a well-known adhesive. As described above, since the outer diameter of the holder 40 is smaller than the diameter of the lumen 11, a gap 13 is formed between the outer circumferential surface of the holder 40 and the inner surface of the lumen 11. The snare wire 30 can be inserted into the gap 13.

The holder 40 is formed of a material having a higher bending elastic modulus than the sheath 10, for example, a metal material such as stainless steel. For this reason, the holder 40 can receive the snare wire 30 without being bent by a force from the snare wire 30, for example, when the snare wire 30 is pulled via the manipulation wire 20.

The snare wire 30 is disposed by the holder 40 as follows. The second wire portion 33 of the snare wire 30 extends through the through-hole 45 of the holder 40 between the second proximal portion 33*a* and the second distal portion 33*b*, and extends across the first wire portion 32. Further, at least a part of the curved portion 34 is disposed on the distal end side relative to the through-hole 45.

To be more specific, the first wire portion 32 of the snare wire 30 extends from the first end 30*a* through the inside of the holder 40 to the distal end side, and is continuous with the curved portion 34. Further, the second wire portion 33 of the snare wire 30 extends from the second end 30*b* through the gap 13 to the distal end side, is curved toward the through-hole 45 of the holder 40, and is inserted through the through-hole 45. Here, the second wire portion 33 extends in the second direction D2 parallel to the through-hole 45 that extends in the second direction D2 perpendicular to the longitudinal axis O1, passes through the through-hole 45, and is continuous with the curved portion 34 across the first wire portion 32. The first wire portion 32 and the second wire portion 33 may be in contact with each other at a position at which the second wire portion 33 crosses the first wire portion 32. The curved portion 34 extends continuously from the first distal portion 32*b* of the first wire portion 32, and is continuous with the second distal portion 33*b* of the second wire portion 33. The curved portion 34 is curved in an approximately circular arc shape between the first distal portion 32*b* of the first wire portion 32 and the second distal portion 33*b* of the second wire portion 33. A size of the loop 31 of the snare wire 30 (an area surrounded by the loop 31) is appropriately set depending on a desired procedure. In this way, a direction in which the snare wire 30 extends is regulated by the through-hole 45 of the holder 40, and thus the snare wire 30 is disposed such that the second wire portion 33 crosses the first wire portion 32.

The manipulator 50 has a rod-like manipulator body 51 that is coupled to the proximal end 10*b* of the sheath 10, and a slider 52 that is slidably mounted on the manipulator body 51. The proximal end 20*b* of the manipulation wire 20 is fixed to the slider 52. The manipulation wire 20 is advanced/ retracted along the longitudinal axis O1 depending on a motion of the slider 52. To be specific, the manipulation wire 20 is moved (retracted) to the proximal end side along the longitudinal axis O1 by moving the slider 52 to the proximal end side relative to the manipulator body 51, and the manipulation wire 20 is moved (advanced) to the distal end side along the longitudinal axis O1 by moving the slider 52 to the distal end side relative to the manipulator body 51. An amount of protrusion of the snare wire 30 from the sheath 10 can be adjusted by the advancing/retracting motion of the manipulation wire 20.

Figure 5:
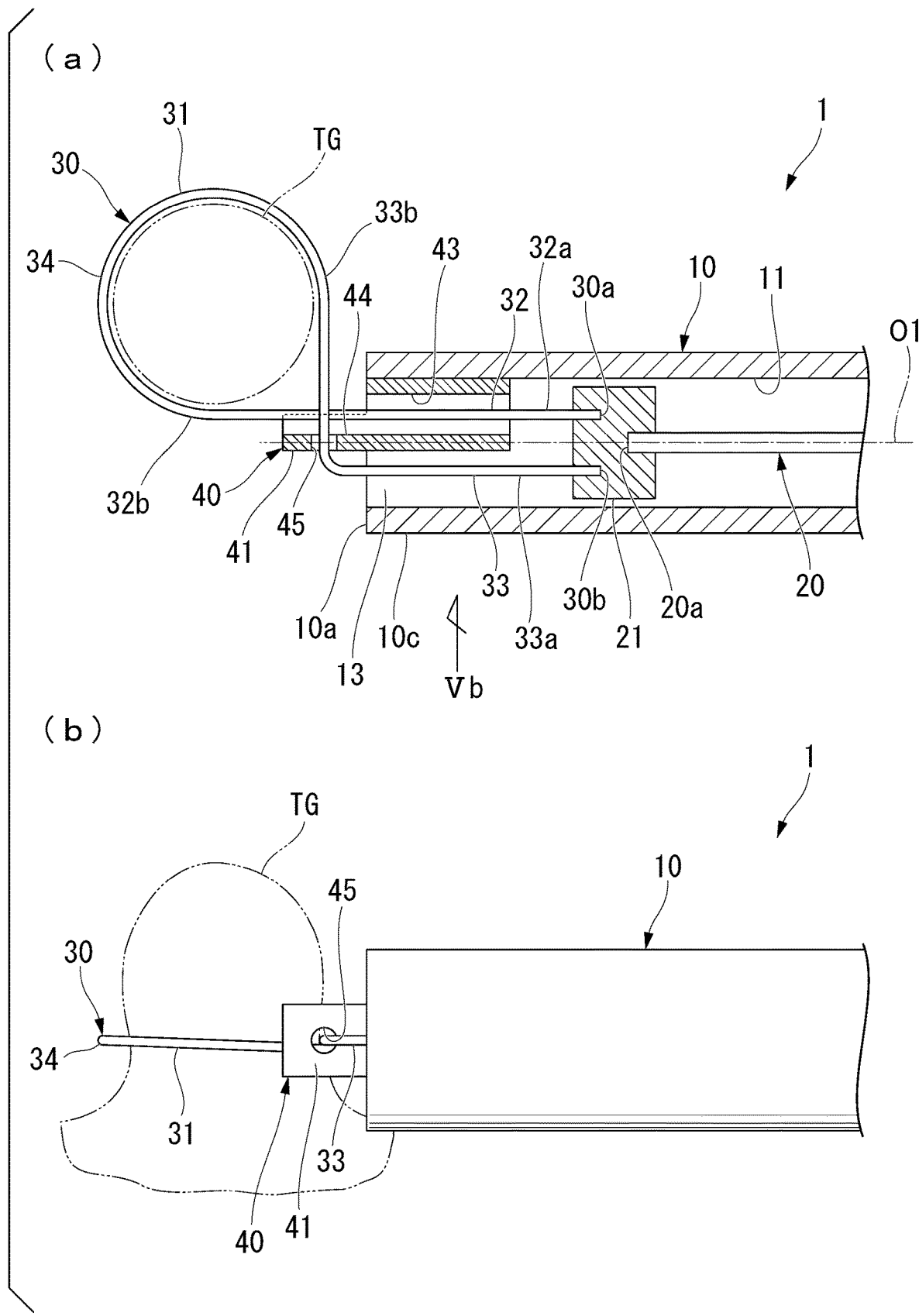
FIG. 5 is a view showing a motion of the snare in use.
Figure 6:
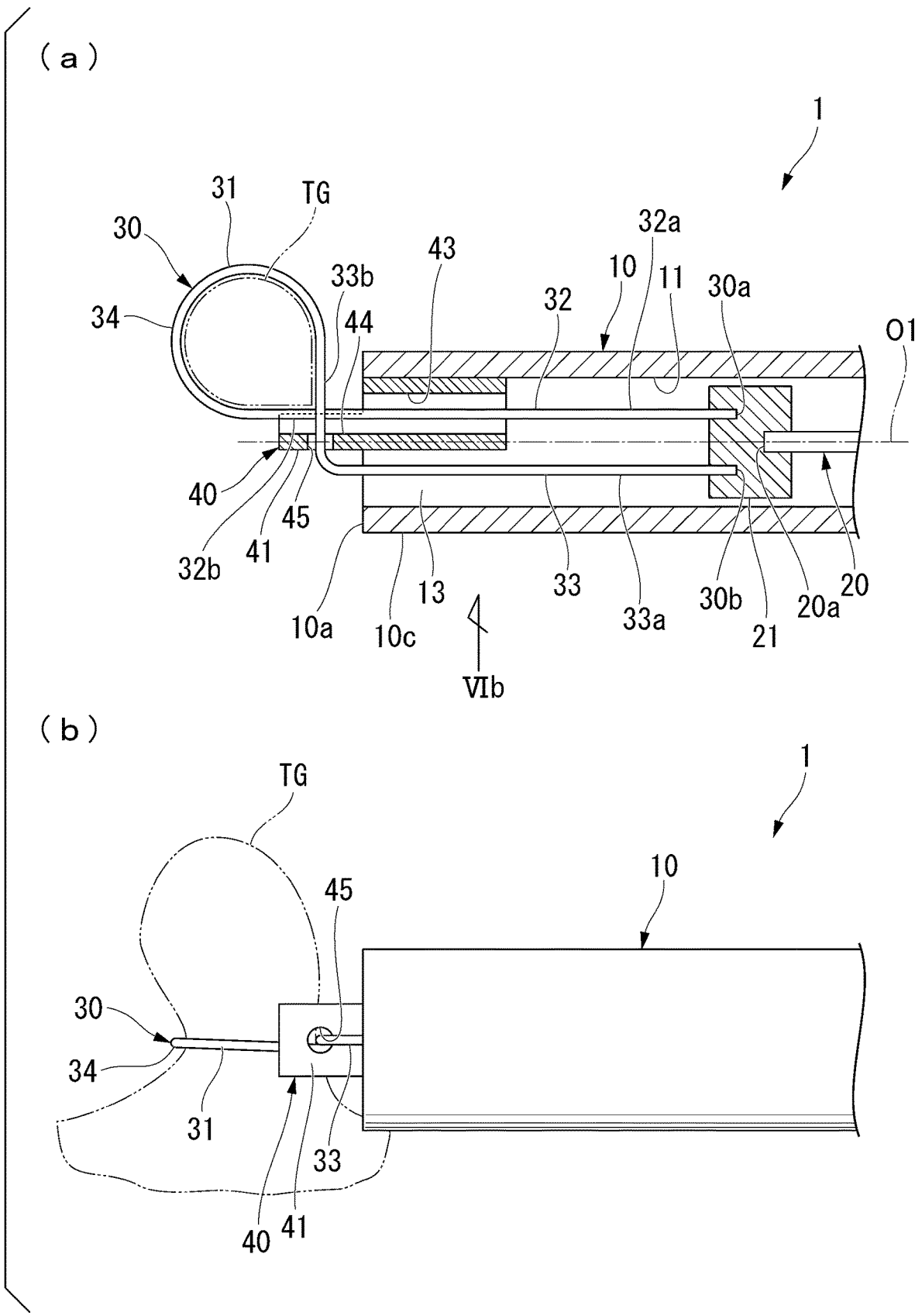
FIG. 6 is a view showing a motion of the snare in use.

Next, a motion of the snare 1 in use will be described with reference to FIGS. 5 and 6. FIGS. 5 and 6 are views showing a motion of the snare 1 in use. FIG. 5(a) is a side sectional view showing a state where target tissue TG is surrounded by the snare wire 30 of the snare 1, and FIG. 5(b) is a view taken from an arrow Vb in FIG. 5(a). Further, FIG. 6(a) is a side sectional view showing a state where target tissue TG is tied with the loop 31 of the snare wire 30, and FIG. 6(b) is a view taken from an arrow VIb in FIG. 6 (a).

First, a user inserts an endoscope (not shown) into a body cavity of a patient from a natural opening of the patient such as the anus or the mouth. The endoscope includes a treatment tool channel through which the snare 1 can be inserted to be advanceable/retractable, and an image pickup device that can image target tissue TG to be excised in the body cavity. The user guides a distal end of the endoscope to a prescribed position in the body cavity of the patient, and catches the target tissue TG in a field of vision of the image pickup device. Subsequently, the user inserts the snare 1 into the treatment tool channel, and guides the snare 1 into the body cavity of the patient through the treatment tool channel. In this case, the size of the loop 31 of the snare wire 30 protruding from the distal end of the sheath 10 is set to be appropriately small in the snare 1 by moving the slider 52 of the manipulator 50 to the proximal end side relative to the manipulator body 51 to retract the manipulation wire 20.

After the distal end of the snare 1 is guided to the vicinity of the target tissue TG through the treatment tool channel, the user moves the slider 52 of the manipulator 50 to the distal end side relative to the manipulator body 51 to advance the manipulation wire 20, and thus increases the size of the loop 31 of the snare wire 30 protruding from the distal end of the sheath 10 to a size that can surround the target tissue TG. The user appropriately manipulates the endoscope to adjust a position of the snare wire 30 such that, as showned in FIG. 5, the loop 31 of the snare wire 30 is wrapped around the target tissue TG. Subsequently, the user moves the slider 52 of the manipulator 50 to the proximal end side relative to the manipulator body 51 from the state showned in FIG. 5, and retracts the manipulation wire 20, that is, pulls the manipulation wire 20. Thus, the first and second wire portions 32 and 33 of the snare wire 30 moves to the proximal end side of the sheath 10, and the size of the loop 31 is reduced. In this case, since the target tissue TG is inserted into the loop 31 of the snare wire 30, the loop 31 comes into contact with an outer surface of the target tissue TG. Furthermore, as the first and second wire portions 32 and 33 of the snare wire 30 move to the proximal end side of the sheath 10 by pulling the manipulation wire 20, the target tissue TG is constricted by the loop 31 of the snare wire 30 as shown in FIG. 6. In this case, since the direction in which the snare wire 30 extends is regulated by the through-hole 45 of the holder 40, a state where the second wire portion 33 of the snare wire 30 crosses the first wire portion 32 is maintained in the same way as before the target tissue TG is constricted.

In a state where the target tissue TG is constricted by the snare wire 30, the user manipulates the manipulator 50 to further pull the manipulation wire 20. Thus, the size of the loop 31 of the snare wire 30 is further reduced, and the target tissue TG is excised. Afterward, by taking the excised target tissue TG out of the body using a well-known tissue collecting device (not shown), and removing the snare 1 from the body cavity, the series of procedures is finished.

The snare 1 can include a sheath 10 configured to have a lumen 11 extending along a longitudinal axis O1; a manipulation wire 20 configured to extend along the longitudinal axis O1 and disposed in the lumen 11 to be movable along the longitudinal axis O1; a snare wire 30 coupled to a distal end 20a of the manipulation wire 20, configured to protrude from the sheath 10, and configured such that an amount of protrusion from the sheath 10 is adjusted depending on movement of the manipulation wire 20; and a holder 40 provided at a distal portion 10c of the sheath 10 and configured to have a through-hole 45 that opens in a second direction D2 intersecting the longitudinal axis O1. The snare wire 30 includes a first wire portion 32 that has a first proximal portion 32a including a first end 30a of the snare wire 30 and a first distal portion 32b linked to the first proximal portion 32a, a second wire portion 33 that has a second proximal portion 33a including a second end 30b of the snare wire 30 and a second distal portion 33b linked to the second proximal portion 33a, extends through the through-hole 45 between the second proximal portion 33a and the second distal portion 33b, and extends across the first wire portion 32, and a curved portion 34 that extends to be curved between the first distal portion 32b and the second distal portion 33b, is linked to the first distal portion 32b and the second distal portion 33b, and has at least a part disposed on a distal side relative to the through-hole 45.

Since the second wire portion 33 of the snare wire 30 extends across the first wire portion 32, and the curved portion 34 extends to be curved between the first distal portion 32b of the first wire portion 32 and the second distal portion 33b of the second wire portion 33, the loop 31 is defined by the first wire portion 32, the second wire portion 33, and the curved portion 34. Accordingly, an entire circumference of the target tissue TG inserted into the loop 31 is surrounded by the snare wire 30 that forms the loop 31. Here, since the second wire portion 33 extends through the through-hole 45, a direction in which the second wire portion 33 extends is regulated by the through-hole 45. For this reason, when the manipulation wire 20 is pulled in a state where the target tissue TG is surrounded by the loop 31, the size of the loop 31 is reduced while maintaining a state where the second wire portion 33 crosses the first wire portion 32, and thus the target tissue TG is constricted by the snare wire 30. In this case, since the snare wire 30 surrounds the entire circumference of the target tissue TG, a force can be applied to the target tissue TG from the entire circumference of the target tissue TG in a direction in which the target tissue TG is constricted. Thus, a sufficient constricting force can be applied to the target tissue TG.

In addition, when the target tissue TG is constricted by the snare 1, the distal end 10a of the sheath 10 is not pressed against the snare wire 30 and the target tissue TG, and thus a force applied in a direction in which the sheath 10 is compressed against the distal end 10a of the sheath 10 can be considerably reduced.

Further, the through-hole 45 of the holder 40 is disposed on the distal side relative to the distal end 10a of the sheath 10. For this reason, the curved portion 34 linked from the second distal portion 33b of the second wire portion 33 of the snare wire 30 extending through the through-hole 45 can be easily disposed apart from the distal end 10a of the sheath 10. That is, the loop 31 of the snare wire 30 can be easily disposed apart from the distal end 10a of the sheath 10. As a result, since the loop 31 can be prevented from coming into contact with the sheath 10, the loop 31 can be easily enlarged and reduced. In addition, part of a constricting force applied to the loop 31 during constriction of the target tissue can be prevented from escaping to the sheath 10 to act on the sheath 10.

The through-hole 45 of the holder 40 can be open in the second direction D2 perpendicular to the longitudinal axis O1, but the present invention is not limited thereto. For example, the through-hole 45 may be open in a direction that is approximately perpendicular to the longitudinal axis O1, be open in a direction that intersects the longitudinal axis O1 at a slightly obtuse angle, or be open in a direction that intersects the longitudinal axis O1 at an acute angle.

Figure 7:
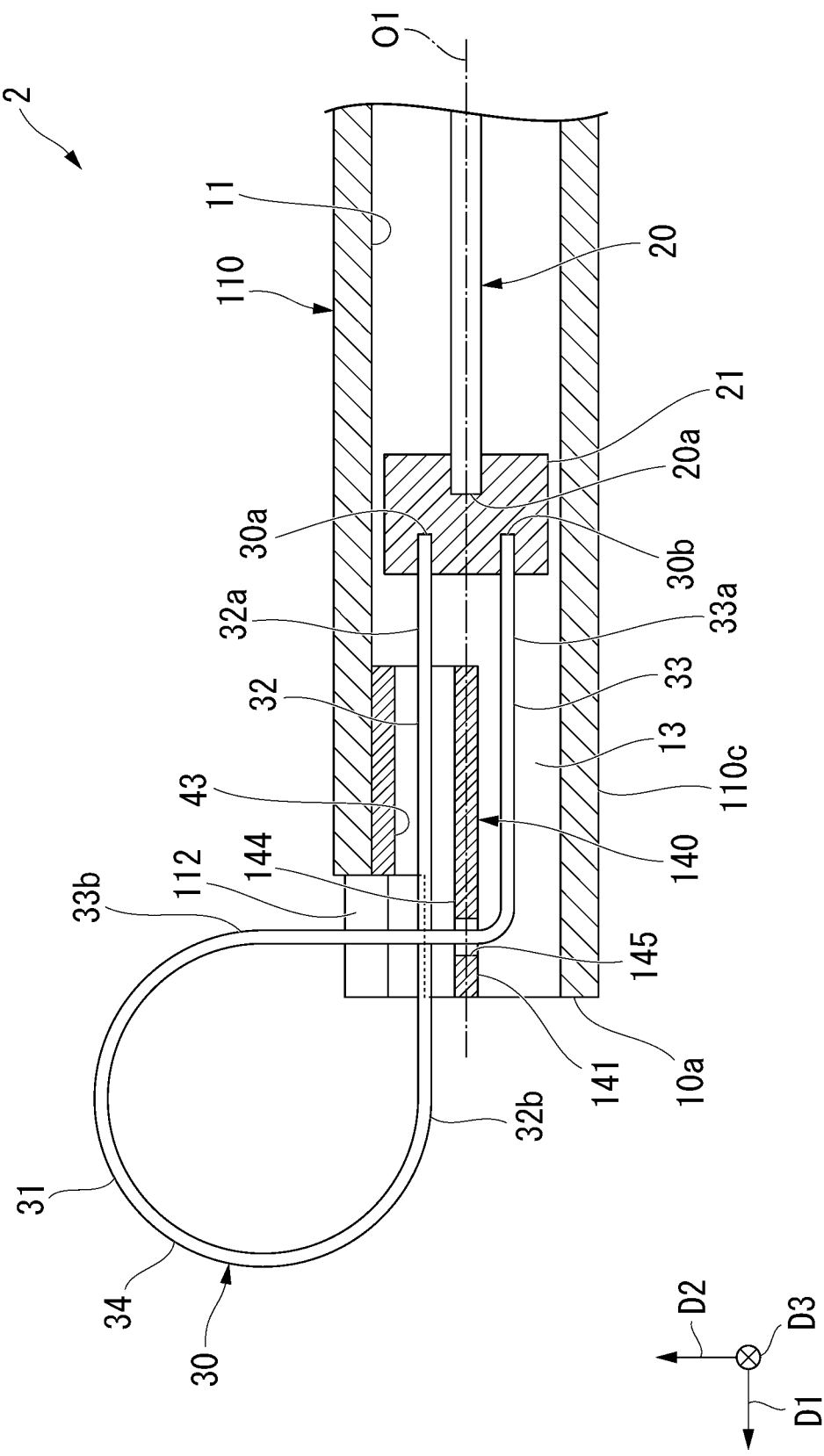
FIG. 7 is a side sectional view showing a distal end side of a snare according to an exemplary embodiment.
Figure 8:
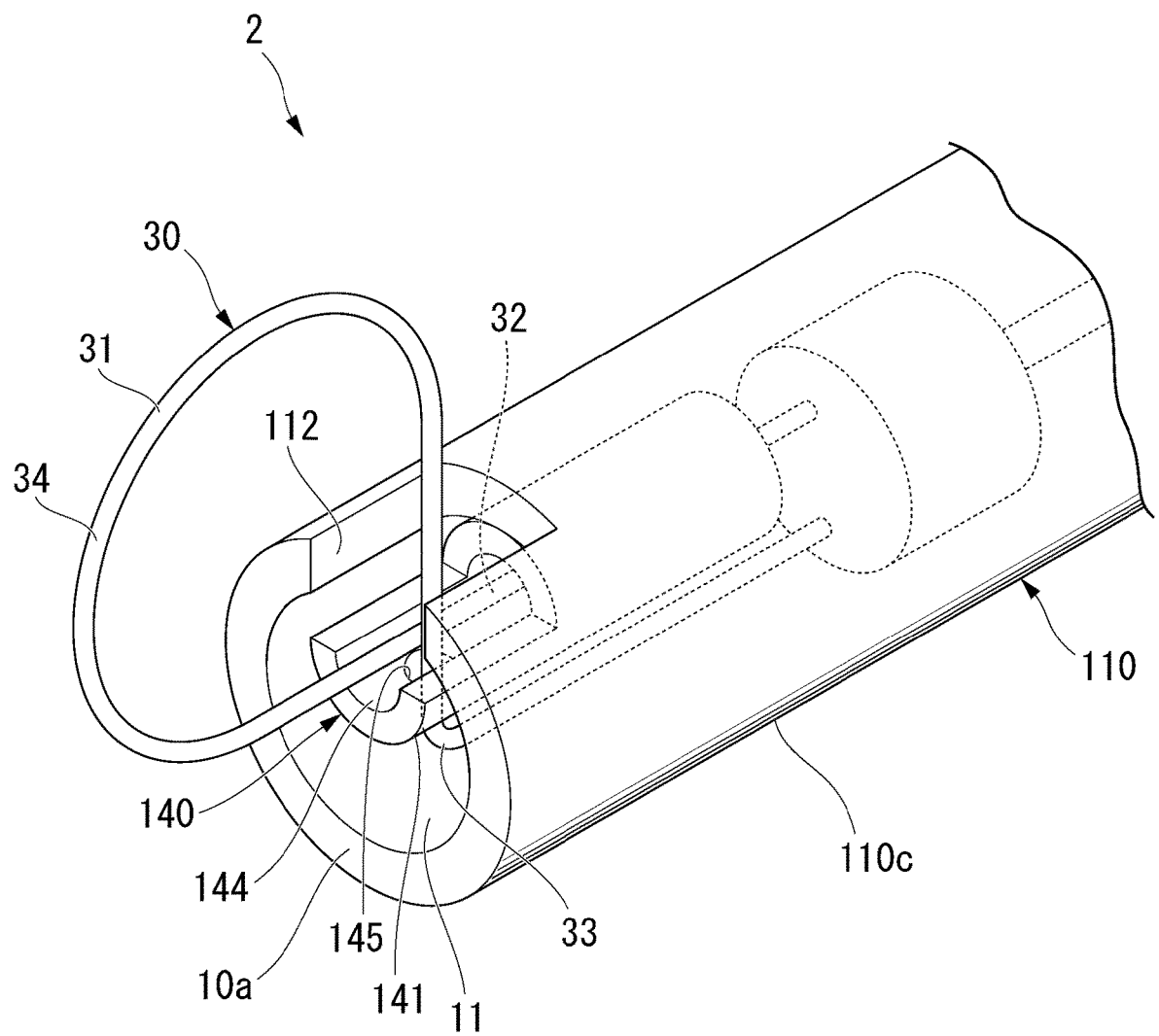
FIG. 8 is a perspective view showing the distal end side of the snare.
Figure 8:
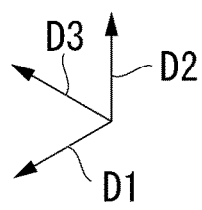

FIG. 7 is a side sectional view showing a distal end side of a snare 2 that is a tissue excision instrument according to an exemplary embodiment. FIG. 8 is a perspective view showing the distal end side of the snare 2. Hereinafter, portions having the same constitution as the snare 1 according to the first embodiment are given the same reference signs, and detailed description thereof is omitted.

The snare 2 can be different in the disposition of the holder from the previously described snare 1. For example, the holder 40 of the snare 1 is disposed such that a part thereof protrudes from the distal end 10a of the sheath 10, whereas a holder 140 of the snare 2 can be fully disposed inside a lumen 11 of a sheath 110. That is, a distal end of the holder 140 is located inside the lumen 11. Further, the sheath 110 of the snare 2 according to the present embodiment is different from the sheath 10 of the snare 1 according to the first embodiment in that a slit 112 is formed in a distal portion 110c of the sheath 110.

The holder 140 has approximately the same shape as the holder 40. The holder 140 is disposed inside the lumen 11 of the sheath 110 such that a position of a distal end of the holder 140 in a direction along a longitudinal axis O1 is coincident with a position of a distal end 10a of the sheath 110. For this reason, an exposed surface 144 and a through-hole 145 that are formed in a distal portion 141 of the holder 140 are disposed inside the lumen 11 of the sheath 110.

The slit 112 is formed in the distal portion 110c of the sheath 110 such that a part of an outer circumferential surface thereof communicates with the lumen 11. A direction in which the slit 112 is open is coincident to a direction (a second direction D2) in which the through-hole 145 passes. A part of the holder 140 is open in a radial direction at a position between the slit 112 and the through-hole 145. The slit 112 communicates with a distal end opening of the distal end 10a of the sheath 110. That is, a distal end of the slit 112 is coincident with the distal end 10a of the sheath 110. In the present embodiment, a length of the slit 112 in a first direction D1 is set to be nearly the same as that of the exposed surface 144 in the first direction D1. Further, a length of the slit 112 in a third direction D3 is set to be nearly the same as that of the distal portion 141 in the third direction D3.

In the snare 2 according to the present embodiment configured in this way, the same effects as the snare 1 according to the first embodiment can be produced. In addition, in the snare 2 according to the present embodiment, the holder 140 formed of a hard material such as a metal material is disposed inside the lumen 11 of the sheath 110. For this reason, since the holder 140 is prevented from directly coming into contact with tissue in a body cavity by the sheath 110, the tissue in the body cavity can be prevented from being damaged by contact of the holder 140.

The holder 140 can be disposed inside the lumen 11 of the sheath 110 such that the position of the distal end of the holder 140 in the direction along the longitudinal axis O1 is coincident with the position of the distal end 10a of the sheath 110, but the present invention is not limited thereto. For example, the holder 140 may be disposed inside the lumen 11 of the sheath 110 such that the distal end of the holder 140 is located slightly on the proximal end side relative to the distal end 10a of the sheath 110.

Further, the slit 112 is formed in the portion that faces the exposed surface 144 of the holder 140 disposed inside the lumen 11 at the distal portion 110c of the sheath 110, but the present invention is not limited thereto. For example, in place of the slit 112 formed in the distal portion 110c of the sheath 110, the through-hole that causes the lumen 11 to communicate with the outside of the sheath 110 may be formed in the distal portion 110c of the sheath 110. In this case, the through-hole formed in the distal portion 110c may be disposed approximately coaxially with the through-hole 145 of the holder 140, and the snare wire 30 inserted through the through-hole 145 may be configured to be insertable.

Figure 9:
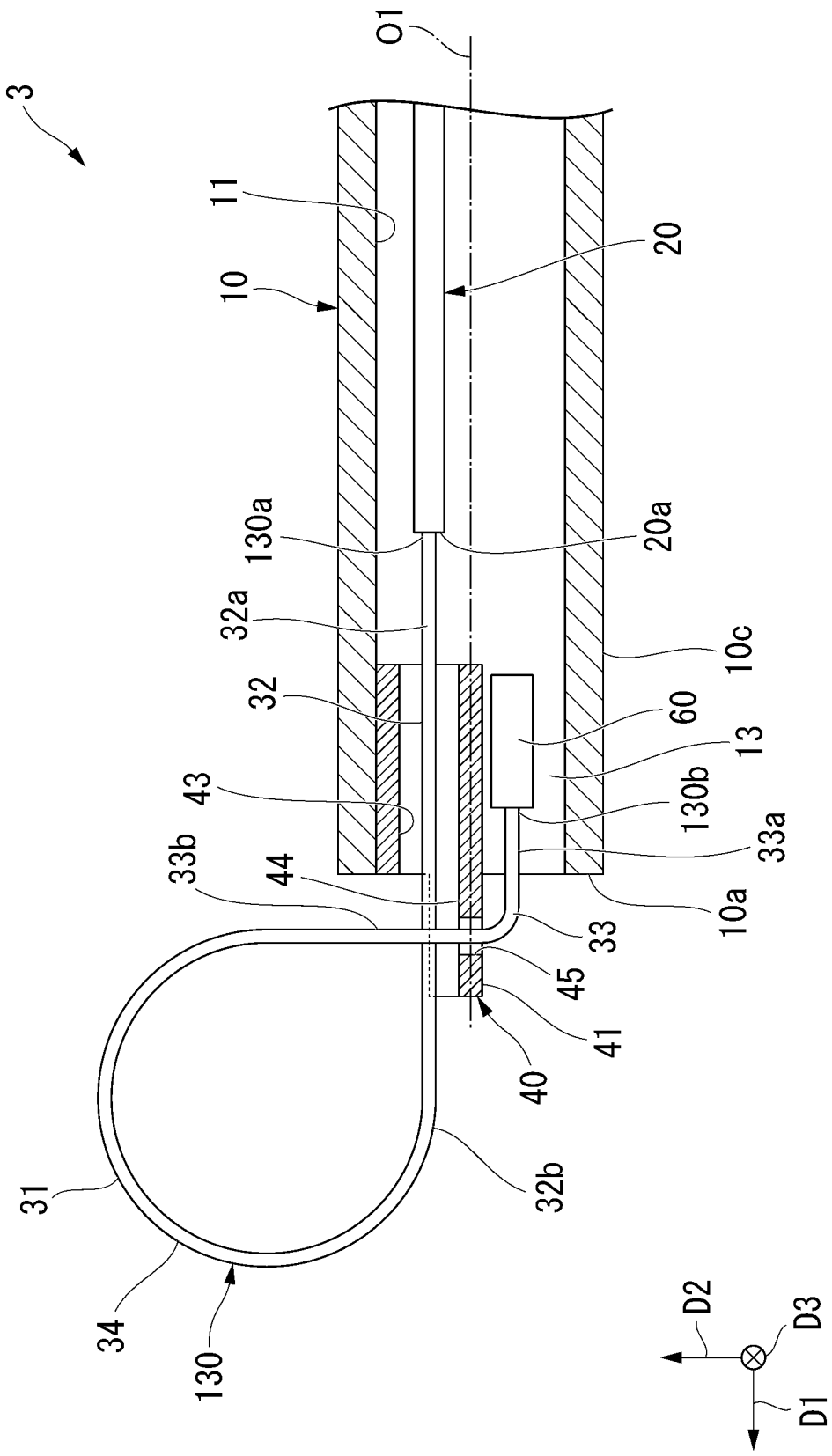
FIG. 9 is a side sectional view showing a distal end side of a snare according to an exemplary embodiment.
Figure 10:
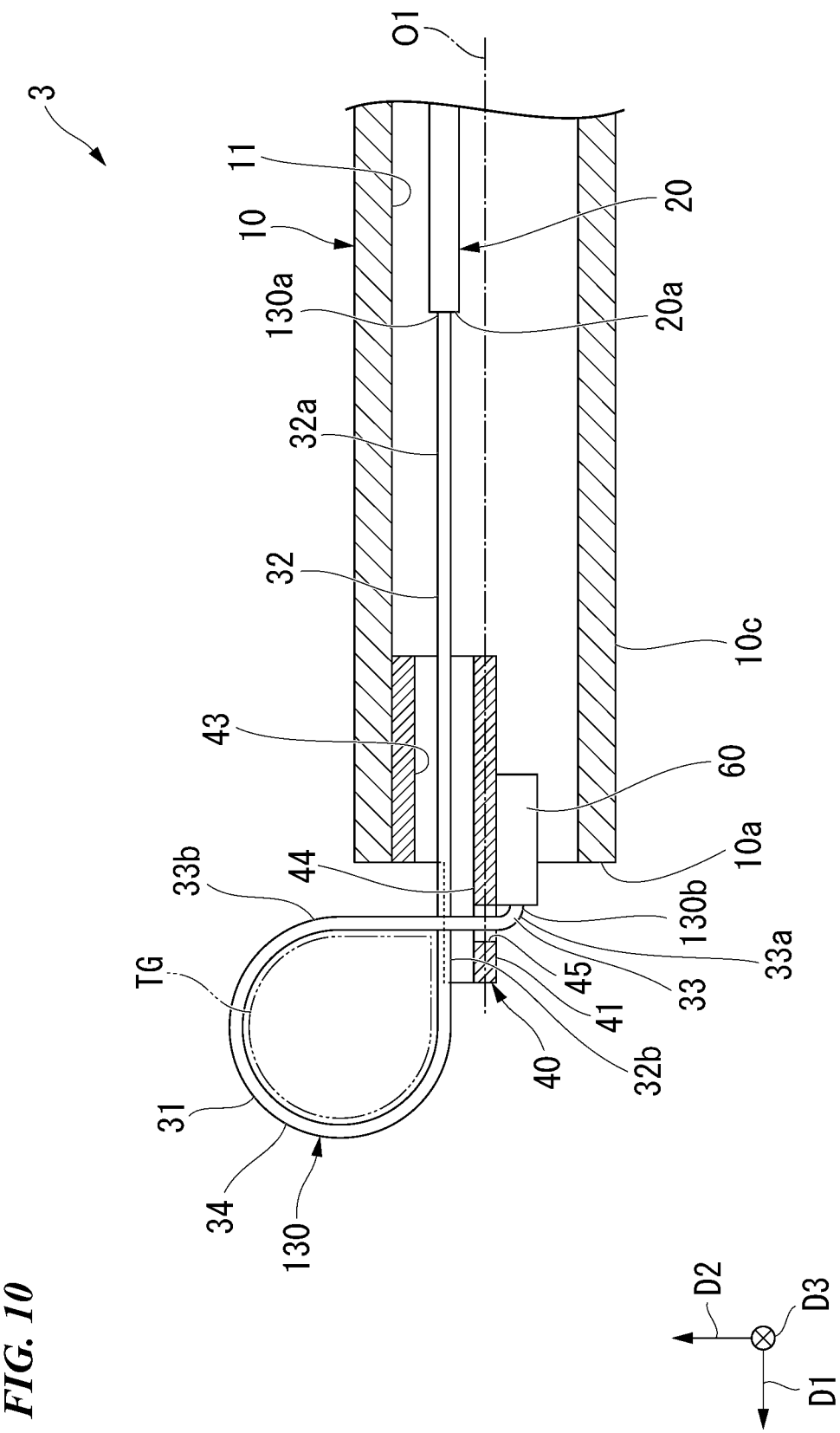
FIG. 10 is a side sectional view showing a motion of the snare in use.

FIG. 9 is a side sectional view showing a distal end side of a snare 3 that is a tissue excision instrument according to an exemplary embodiment. FIG. 10 is a side sectional view showing a motion of the snare 3 in use.

The snare 3 can be configured such that one end of a snare wire is coupled to a stopper. The snare 3 has a stopper 60 that is disposed in a distal portion 10c of a sheath 10 and has external lengths in which the stopper 60 cannot be inserted into a through-hole 45 of a holder 40. The stopper 60 can be disposed inside a lumen 11 of the sheath 10 to be parallel to the holder 40 in a second direction D2. Further, the stopper 60 is formed in a rod shape that extends along a longitudinal axis O1. The stopper 60 has external lengths in which it is movable along the longitudinal axis O1 in a gap 13 between an outer circumferential surface of the holder 40 and an inner surface of the lumen 11 (an inner surface of the sheath 10) in the lumen 11 of the sheath 10. At least a part of the stopper 60 preferably has a contour larger than an opening of the through-hole 45 of the holder 40. In this way, the stopper 60 is configured such that it cannot be inserted through the through-hole 45. The stopper 60 is formed of, for example, a metal material such as stainless steel.

A first end 130a of a snare wire 130 of the snare 3 is coupled to a distal end 20a of a manipulation wire 20. In the snare 1 according to the first embodiment, the first and second ends 30a and 30b of the snare wire 30 are coupled to the distal end 20a of the manipulation wire 20 via the coupler 21. However, in the snare 3 according to the present embodiment, the first end 130a of the snare wire 130 is directly fixed to the distal end 20a of the manipulation wire 20 by brazing or welding. Further, a second end 130b of the snare wire 130 is coupled to the stopper 60. In the present embodiment, the second end 130b of the snare wire 130 is fixed to the stopper 60 by brazing or welding.

Next, a motion of the snare 3 will be described. Since a first wire portion 32 of the snare wire 130 is pulled when the manipulation wire 20 is pulled, the stopper 60 is pulled toward the through-hole 45 of the holder 40 by a second wire portion 33 of the snare wire 130 while reducing a size of a loop 31 of the snare wire 130 as showned in FIG. 10. As described above, since the stopper 60 is configured such that it cannot be inserted through the through-hole 45, when the manipulation wire 20 is further pulled, the stopper 60 is caught in the through-hole 45, and is no more moved. Accordingly, when the manipulation wire 20 is further pulled from this state, only the size of the loop 31 is reduced. Thus, hereinafter, like the snare 1 according to the first embodiment, target tissue TG can be constricted and excised.

In the snare 3, the same effects as the snare 1 according to the first embodiment can be produced.

The stopper 60 can be configured to move in the lumen 11 of the sheath 10 along the longitudinal axis O1, but the present invention is not limited thereto. For example, the stopper 60 may be fixed to an outer circumferential surface of the holder 40 in the lumen 11 by welding or the like. Thus, since the second end 130b of the snare wire 130 is fixed to the holder 40, the manipulation wire 20 to which the first end 130a of the snare wire 130 is coupled is pulled, so that the size of the loop 31 of the snare wire 130 can be reduced, and the target tissue TG can be constricted. In this case, the constitution of the stopper 60 is not particularly limited as long as the second end 130b of the snare wire 130 is configured to be able to be fixed to the holder 40.

Further, the first end 130a of the snare wire 130 is coupled to the distal end 20a of the manipulation wire 20, and the second end 130b of the snare wire 130 is coupled to the stopper 60, but the present invention is not limited thereto. The first end 130a of the snare wire 130 may also be coupled to the stopper, and the second end 130b of the snare wire 130 may be coupled to the distal end 20a of the manipulation wire 20. In this case, the stopper coupled to the first end 130a of the snare wire 130 may be disposed on a proximal end side of the holder 40, and may have external lengths larger than an inner diameter of the holder 40. In this constitution, when the manipulation wire 20 is pulled, the second wire portion 33 of the snare wire 130 is pulled, the stopper is pulled toward a proximal end of the holder 40 by the first wire portion 32 while reducing the size of the loop 31. Thus, the stopper is caught in the holder 40, and is fixed to the holder 40. The manipulation wire 20 is further pulled from this state, so that, like the snare 3 according to the aforementioned third embodiment, the size of the loop 31 can be reduced, and the target tissue TG can be constricted.

Figure 11:
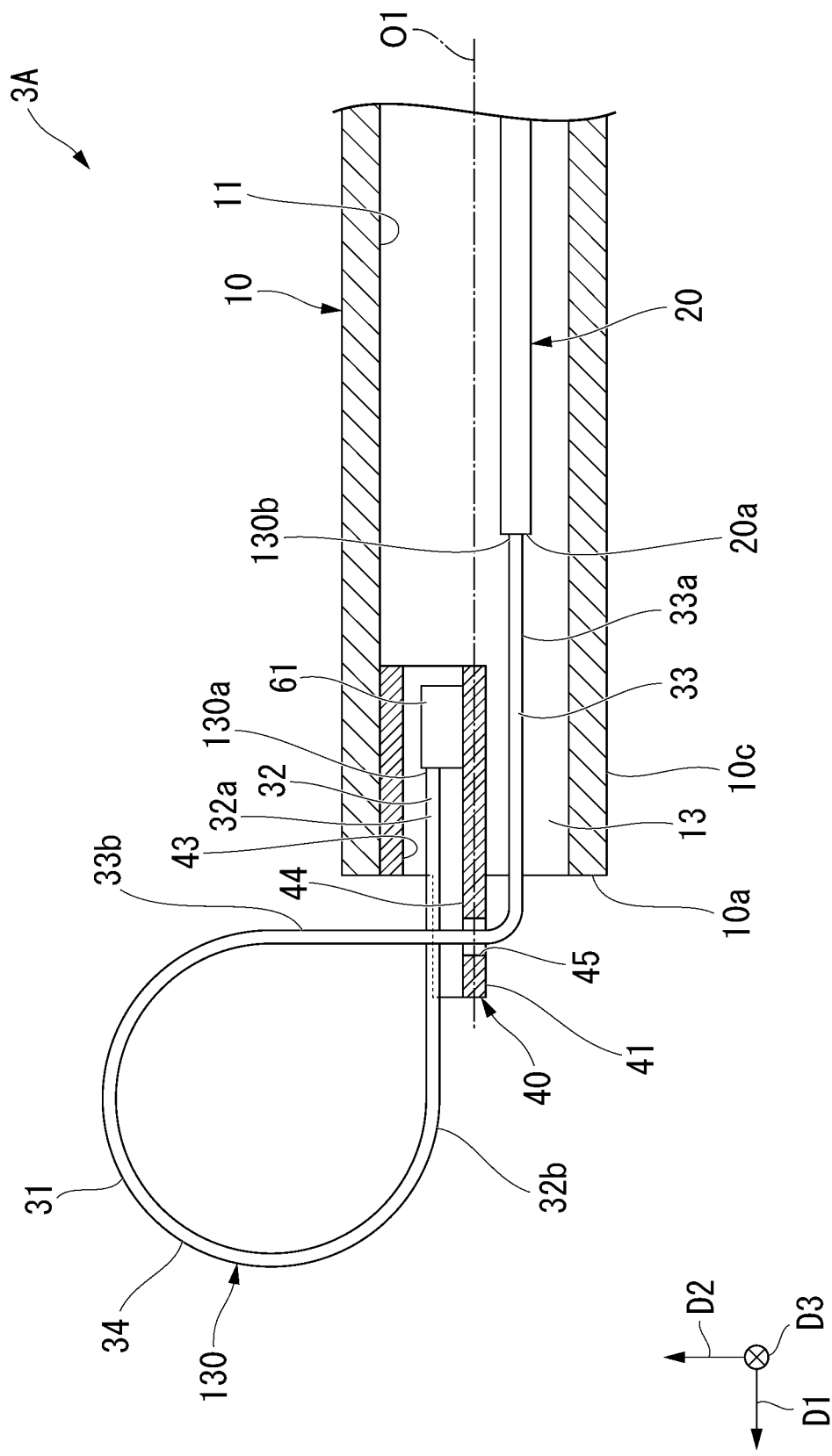
FIG. 11 is a side sectional view showing a modification of the snare.

Furthermore, the stopper coupled to the first end 130a of the snare wire 130 may be fixed to the holder 40. In this case, like a snare 3A shownned in FIG. 11, the stopper 61 may be disposed on a hollow forming surface 43 of the holder 40 rather than the proximal end side of the holder 40. The stopper 61 is fixed to the hollow forming surface 43 by welding or the like. The constitution of the stopper 61 is not particularly limited as long as the first end 130a of the snare wire 130 is configured to be able to be fixed to the holder 40. In this constitution, since the first end 130a of the snare wire 130 is fixed to the holder 40, the manipulation wire 20 to which the second end 130b of the snare wire 130 is pulled, so that the size of the loop 31 of the snare wire 130 can be reduced, and the target tissue TG can be constricted.

In the snare 1, both the first end 30a and the second end 30b of the snare wire 30 are coupled to the manipulation wire 20. However, only one of the first end 130a and the second end 130b of the snare wire 130 may be coupled to the manipulation wire 20.

Figure 12:
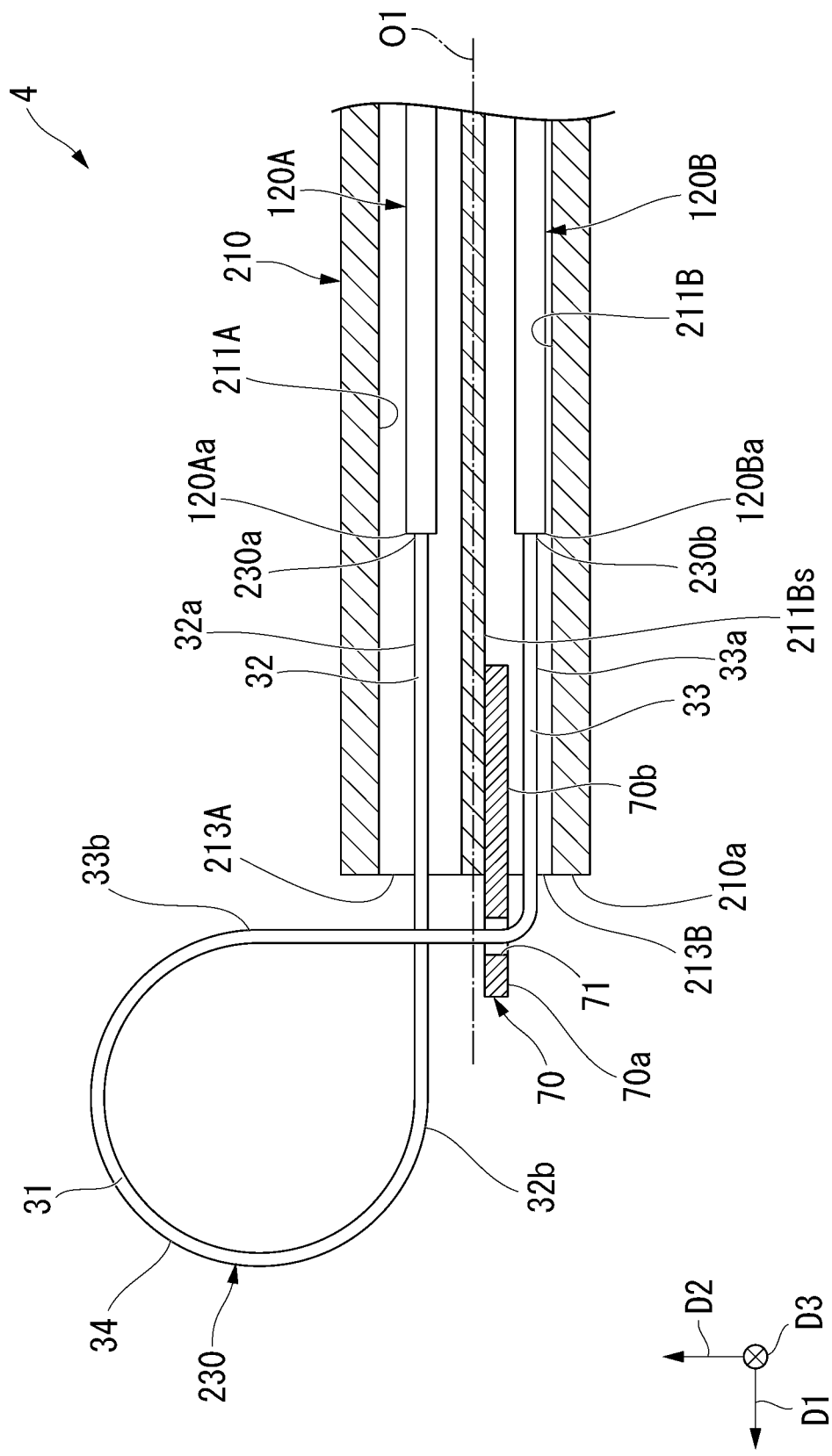
FIG. 12 is a side sectional view showing a distal end side of a snare according to an exemplary embodiment.
Figure 13:
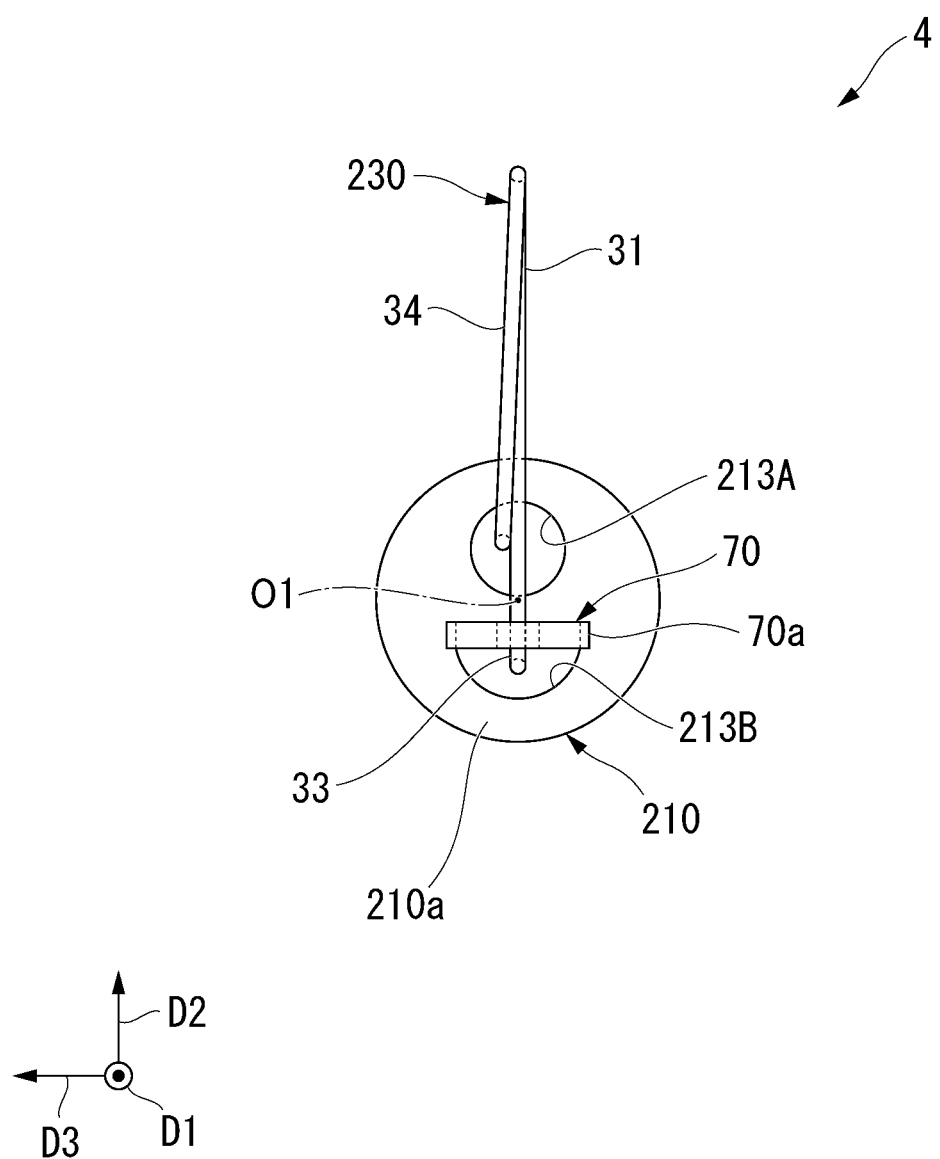
FIG. 13 is a front view showing the distal end side of the snare.
Figure 14:
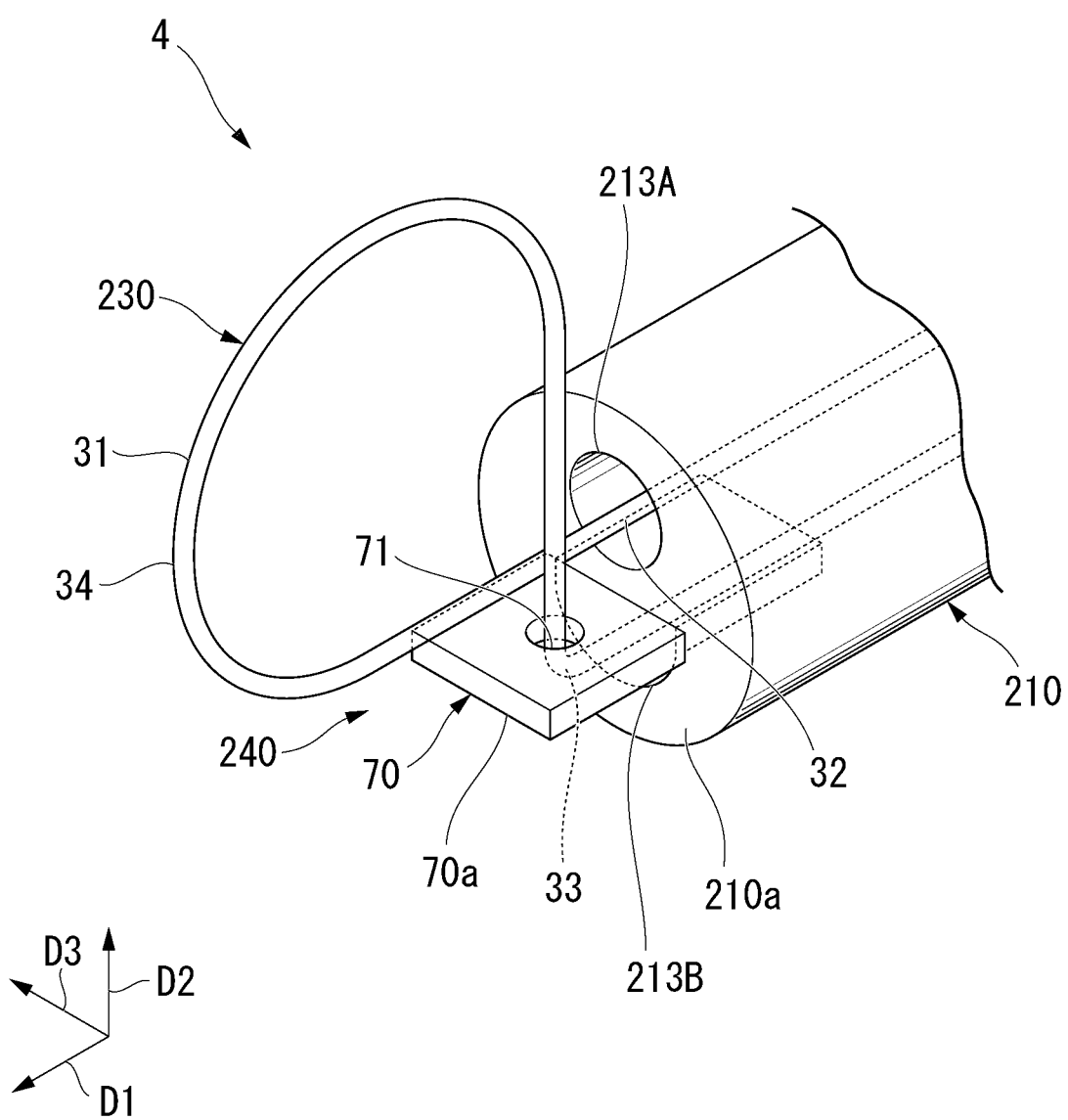
FIG. 14 is a perspective view showing the distal end side of the snare.

FIG. 12 is a side sectional view showing a distal end side of a snare 4 that is a tissue excision instrument according to the present embodiment. FIG. 13 is a front view showing the distal end side of the snare 4. FIG. 14 is a perspective view showing the distal end side of the snare 4. The snare 4 according to the present embodiment is different in the constitutions of the sheath and the holder from the snare 1 according to the first embodiment. Hereinafter, portions having the same constitution as the snare 1 according to the first embodiment are given the same reference signs, and detailed description thereof is omitted.

A sheath 210 of the snare 4 is a multi-lumen tube, and has a first lumen 211A and a second lumen 211B. Like the lumen 11 according to first embodiment, the first lumen 211A and the second lumen 211B extend from a distal end 210a to a proximal end of the sheath 210 along a longitudinal axis O1, and are open to the distal end 210a of the sheath 210. Thus, a first distal end opening 213A is formed in a distal end of the first lumen 211A, and a second distal end opening 213B is formed in a distal end of the second lumen 211B. Further, a central axis of the first lumen 211A and a central axis of the second lumen 211B are disposed to be parallel to a second direction D2. A sectional shape perpendicular to the longitudinal axis O1 of the first lumen 211A is a circular shape. A sectional shape perpendicular to the longitudinal axis O1 of the second lumen 211B is a semi-circular shape having a chord perpendicular to the second direction D2, and bulges in a direction away from the first lumen 211A.

A regulating member 70 is mounted in the second distal end opening 213B of the second lumen 211B. The regulating member 70 is formed in a plate shape that has a plane perpendicular to the second direction D2. A distal portion 70a of the regulating member 70 is disposed to protrude from the distal end 210a of the sheath 210 to a distal end side. A proximal portion 70b of the regulating member 70 is inserted into the second lumen 211B of the sheath 210, and is fitted into the second distal end opening 213B of the second lumen 211B. Further, a proximal portion 70b of the regulating member 70 is disposed on an inner plane 211Bs perpendicular to the second direction D2 in the second lumen 211B, and is fixed to the inner plane 211Bs by a well-known adhesive. A gap through which a snare wire 230 can be inserted is formed between the proximal portion 70b of the regulating member 70 and an inner circumferential surface of the second lumen 211B which faces the inner plane 211Bs. A length of the distal portion 70a of the regulating member 70 in a third direction D3 is set to be larger than that of the proximal portion 70b in the third direction D3. The regulating member 70 is formed of, for example, a metal material such as stainless steel.

A through-hole 71 passing through the distal portion 70a in the second direction D2 is formed in the distal portion 70a of the regulating member 70. An inner diameter of the through-hole 71 is set to be slightly larger than an outer diameter of the snare wire 230. In the present embodiment, the regulating member 70 having the through-hole 71 corresponds to the holder.

Unlike the snare 1 according to the first embodiment, the snare 4 according to the present embodiment includes two manipulation wires, namely a first manipulation wire 120A and a second manipulation wire 120B. The first manipulation wire 120A and the second manipulation wire 120B have approximately the same constitution as the manipulation wire 20 according to the first embodiment. The first manipulation wire 120A is movably inserted through the first lumen 211A of the sheath 210. The second manipulation wire 120B is movably inserted through the second lumen 211B of the sheath 210. The first manipulation wire 120A and the second manipulation wire 120B can be separately advanced/retracted along the longitudinal axis O1 by a manipulator (not shown) coupled to the proximal end of the sheath 210.

The first end 230a of the snare wire 230 of the snare 4 is inserted into the first lumen 211A of the sheath 210, and is coupled to a distal end 120Aa of the first manipulation wire 120A. Further, the second end 230*b* of the snare wire 230 is inserted into the second lumen 211B of the sheath 210, and is coupled to a distal end 120Ba of the second manipulation wire 120B. The first end 230*a* of the snare wire 230 is fixed to the distal end 120Aa of the first manipulation wire 120A by brazing or welding. Similarly, the second end 230*b* of the snare wire 230 is fixed to the distal end 120Ba of the second manipulation wire 120B by brazing or welding.

Like the snare wire 30 according to the first embodiment, the snare wire 230 is configured such that a second wire portion 33 extends through a through-hole 71 between a second proximal portion 33*a* and a second distal portion 33*b* and extends across a first wire portion 32.

In the snare 4 configured in this way, like the snare 1 according to the first embodiment, by pulling both the first manipulation wire 120A and the second manipulation wire 120B using the manipulator (not shown), or by fixing one of them and pulling the other, a size of the loop 31 of the snare wire 230 can be reduced while maintaining a state where the second wire portion 33 of the snare wire 230 crosses the first wire portion 32. Accordingly, in the snare 4 according to the present embodiment, the same effects as the snare 1 according to the first embodiment can be produced.

While the preferred embodiments of the present invention have been described, the present invention is not limited to these embodiments. Additions, omissions, substitutions, and other modifications of the constitution are possible without departing from the spirit of the present invention.

What is claimed is:

1. A tissue excision instrument comprising:
   a sheath including a lumen extending along a longitudinal axis;
   a manipulation wire that extends along the longitudinal axis and that is provided within the lumen, the manipulation wire being configured to move along the longitudinal axis;
   a snare wire coupled to a distal end of the manipulation wire, the snare wire being configured to protrude from the sheath, an amount of protrusion from the sheath being adjusted based on movement of the manipulation wire; and
   a holder mounted on a distal portion of the sheath including a through-hole that opens in a direction that intersects the longitudinal axis, wherein:
   a portion of the snare wire extends through the through hole, and
   the snare wire includes:
      a first wire portion that extends through an opening on a distal-most end of the sheath; and
      a second wire portion that extends through the through-hole.

2. The tissue excision instrument according to claim 1, wherein the through-hole is disposed more distally than a distal end of the sheath.

3. The tissue excision instrument according to claim 2, further comprising a stopper disposed inside the sheath, the stopper having a dimension that is larger than the through-hole,
   wherein a first end of the snare wire is coupled to the distal end of the manipulation member, and
   a second end of the snare wire is coupled to the stopper.

4. The tissue excision instrument according to claim 1, wherein:
   the holder is cylindrical and includes a hollow forming surface that defines an internal space that communicates with the lumen;
   the holder includes an exposed surface, which is a portion of the hollow forming surface that is exposed by a cut out portion of the cylindrical holder; and
   the through-hole passes between the exposed surface and an outer circumferential surface of the holder.

5. The tissue excision instrument according to claim 1, wherein the snare wire includes:
   the first wire portion including:
      a first proximal portion that includes a first end of the snare wire; and
      a first distal portion linked to the first proximal portion;
   the second wire portion including:
      a second proximal portion that includes a second end of the snare wire; and
      a second distal portion linked to the second proximal portion, the second wire portion extending through the through-hole located between the second proximal portion and the second distal portion, and intersecting the first wire portion such that the second wire portion extends towards a side of the sheath; and
   a curved portion that curves between the first distal portion and the second distal portion, the curved portion being connected to the first distal portion and the second distal portion, and at least a part of the curved portion being disposed distally of the through-hole, and
   in a side view perpendicular to the longitudinal axis, the through-hole is located between a portion of the second wire portion that intersects the first wire portion and the second proximal portion, and the second wire portion is configured to move in a direction across the first wire portion by moving the manipulation member along the longitudinal axis.

* * * * *